United States Patent [19]

Winn et al.

[11] 4,088,765

[45] May 9, 1978

[54] 5,6-DIMETHOXY-2-HETEROCYCLIC BENZIMIDAZOLES

[75] Inventors: Martin Winn, Deerfield; Jaroslav Kyncl, Lake Bluff, both of Ill.

[73] Assignee: Abbott Laboratories, North Chicago, Ill.

[21] Appl. No.: 746,656

[22] Filed: Dec. 2, 1976

[51] Int. Cl.$^2$ .................. C07D 401/04; A61K 31/47; A61K 31/445
[52] U.S. Cl. ................................ 424/258; 424/267; 260/293.6; 260/286 R; 260/288 CE
[58] Field of Search .................. 260/293.59, 288 CE, 260/293.6, 286 R; 424/267, 258

Primary Examiner—Jose Tovar
Attorney, Agent, or Firm—Gildo E. Fato; Robert L. Niblack

[57] ABSTRACT

Described are the compounds 5,6-dimethoxy-2-(4-benzyl-1-piperidino) benzimidazole and 5,6-dimethoxy-2 (6,7-dimethoxy-1,2,3,4-tetrahydro 2-isoquinolinyl benzimidazole and pharmaceutically acceptable acid addition salts thereof. The compounds are useful as antihypertensive agents.

9 Claims, No Drawings

5,6-DIMETHOXY-2-HETEROCYCLIC BENZIMIDAZOLES

BACKGROUND OF THE INVENTION

This invention relates to new and useful compounds particularly useful as chemotherapeutic agents valuable in reducing blood pressure in hypertensive subjects.

SUMMARY OF THE INVENTION

The present invention relates to new benzimidazole compounds active as antihypertensive agents and of the formulae:

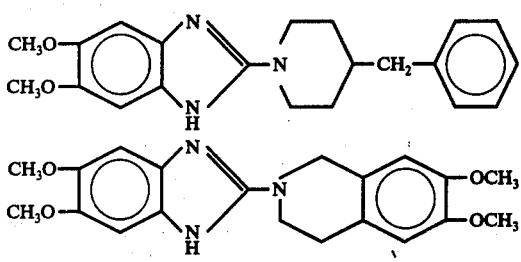

DETAILED DESCRIPTION OF THE INVENTION

The compounds of this invention are particularly effective in reducing blood pressure in hypertensive mammals. The antihypertensive effect of the hydrochloride salts of the compounds of formulae I and II were screened in spontaneously hypertensive (SH) rats as described in copending application Ser. No. 621,980 filed Oct. 14, 1975 and found to effect a reduction in blood pressure of from 20 to 40% when administered intraperitoneally at a dosage level of 30 milligrams per kilogram (mg/kg).

| HCl Compound Formula: | Percent Change at: | | |
|---|---|---|---|
| | 1 Hour | 3 Hours | 5 Hours |
| I | 20,17 | | |
| II | 10,31 | 40,34 | 19,24 |

The compounds are effective at dosages generally from 1 to 500 milligrams daily.

The compounds of this invention can be prepared as described in the following examples.

EXAMPLE I 5,6-dimethoxy-2-(4-benzyl-1-piperidino) benzimidazole hydrochloride 3.00 g 2-chloro 5,6 dimethoxy benzimidazole [(Lit ref. Il. Farmaco. 28 (2) 164) 1973]. 5.75 g 4-benzyl piperidine and 20 ml. 2-methoxyethanol were reflexed 7 hours. The solvent was removed in vacuo and a water solution of potassium bicarbonate was added. The solid which formed was filtered, washed with water and dissolved in chloroform. The chloroform extract was dried over magnesium sulfate and concentrated. The residue was treated with ether in which the product formed an unsoluble gum. This was dissolved in isopropyl alcohol and acidified with HCl giving 4.34 g (78%) desired product mp 265°–267° decomp.

Anal for $C_{25}H_{25}N_3O_2$—HCl: C=62.14, H=6.95, N=10.35, Cl=8.73; Found: C=62.08, H=6.92, N=10.60, Cl=8.36.

EXAMPLE II 5,6-Dimethoxy-2 (6,7-dimethoxy-1,2,3,4-tetrahydro 2-isoquinolinyl benzimidazole hydrochloride 2.60 g 2-chloro-5,6-dimethoxy benzimidazole, 5.50 g 6,7-dimethoxy 1,2,3,4-tetrahydro isoquinoline, and 30 ml. 2-methoxyethanol were reflexed 7 hours and the reaction ran as described in Example I to give 3.67 g of the hydrochloride salt, mp. 275°–277° decomp (74% yield).

Anal for $C_{20}H_{23}N_3O_4.HCl$: C=56.67, H=6.18, N=9.91; Found: C=56.60, H=5.84, N=10.07.

What is claimed is:

1. A compound selected from the group consisting of 5,6-dimethoxy-2-(4-benzyl-1-piperidino) benzimidazole and 5,6-dimethoxy-2(6,7-dimethoxy-1,2,3,4-tetrahydro 2-isoquinolinyl) benzimidazole and pharmaceutically acceptable acid addition salts thereof.
2. A compound in accordance with claim 1: 5,6-dimethoxy 2-(4-benzyl-1-piperidino) benzimidazole hydrochloride.
3. A compound in accordance with claim 1: 5,6-dimethoxy-2-(6,7-dimethoxy-1,2,3,4-tetrahydro-2-isoquinolinyl) benzimidazole hydrochloride.
4. A pharamceutical composition comprising a therapeutically effective amount of a compound selected from the group consisting of 5,6-dimethoxy 2-(4-benzyl-1-piperidino) benzimidazole and 5,6-dimethoxy-2-(6,7-dimethoxy-1,2,3,4-tetrahydro 2-isoquinolinyl) benzimidazole and pharmaceutically acceptable acid addition salts thereof and a pharmaceutically acceptable carrier.
5. The composition of claim 4 wherein the compound is 5,6-dimethoxy-2-(4-benzyl-1-piperidino) benzimidazole and pharmaceutically acceptable acid addition salts thereof.
6. The composition of claim 4 wherein the compound is 5,6-dimethoxy-2-(6,7-dimethoxy-1,2,3,4-tetrahydro 2-isoquinolinyl) benzimidazole and pharmaceutically acceptable acid addition salts thereof.
7. A method of treating hypertension in a mammal comprising administering to a mammal so afflicted, a therapeutically effective amount of a compound selected from the group consisting of 5,6-dimethoxy-2-(4-benzyl-1-piperidino) benzimidazole and 5,6-dimethoxy-2(6,7-dimethoxy-1,2,3,4-tetrahydro 2-isoquinolinyl) benzimidazole and pharmaceutically acceptable acid addition salts thereof.
8. The method of claim 7 wherein said compound is 5,6-dimethoxy-2-(4-benzyl-1-piperidino) benzimidazole.
9. The method of claim 7 wherein said compound is 5,6-dimethoxy-2 (6,7-dimethoxy-1,2,3,4-tetrahydro-2-isoquinolinyl) benzimidazole.

* * * * *